United States Patent [19]  [11] 4,048,196
Broecker et al.  [45] Sept. 13, 1977

[54] MANUFACTURE OF BUTANEDIOL AND/OR TETRAHYDROFURAN FROM MALEIC AND/OR SUCCINIC ANHYDRIDE VIA γ-BUTYROLACTONE

[75] Inventors: Franz Josef Broecker, Ludwigshafen; Matthias Schwarzmann, Limburgerhof, both of Germany

[73] Assignee: BASF Aktiengesellschaft, Ludwigshafen, Germany

[21] Appl. No.: 631,911

[22] Filed: Nov. 14, 1975

[30] Foreign Application Priority Data

Nov. 23, 1974 Germany .............................. 2455617

[51] Int. Cl.² .................... C07D 307/08; C07D 31/18; C07D 29/00
[52] U.S. Cl. .......................... 260/346.11; 260/635 D; 260/343.6; 252/463
[58] Field of Search ................. 260/346.8 R, 346.1 R, 260/635 D, 343.6

[56] References Cited

U.S. PATENT DOCUMENTS

| | | | |
|---|---|---|---|
| 2,772,293 | 11/1956 | Gilbert et al. | 260/346.1 R |
| 2,863,928 | 12/1958 | Indest | 260/635 D |
| 3,370,067 | 2/1968 | Johnson | 260/346.1 R |
| 3,492,314 | 1/1970 | Asano et al. | 260/346.1 R |

FOREIGN PATENT DOCUMENTS 806,025   12/1958   United Kingdom ............ 260/635 D Primary Examiner—Henry R. Jiles
Assistant Examiner—Bernard Dentz
Attorney, Agent, or Firm—Keil, Thompson & Shurtleff

[57] ABSTRACT

A process for the manufacture of 1,4-butanediol and/or tetrahydrofuran, wherein maleic acid or succinic acid is used as the starting material, butyrolactone is produced in defined stages and is hydrogenated to butanediol or tetrahydrofuran, and the by-products formed are in each case recycled to the process.

4 Claims, 2 Drawing Figures

MANUFACTURE OF BUTANEDIOL AND/OR TETRAHYDROFURAN FROM MALEIC AND/OR SUCCINIC ANHYDRIDE VIA γ-BUTYROLACTONE

The present invention relates to a continuous process for the manufacture of butanediol and/or tetrahydrofuran by catalytic hydrogenation of maleic anhydride and/or succinic anhydride (in the former case via succinic anhydride), with the formation of γ-butyrolactone ("butyrolactone") as an intermediate, in accordance with the following equation:

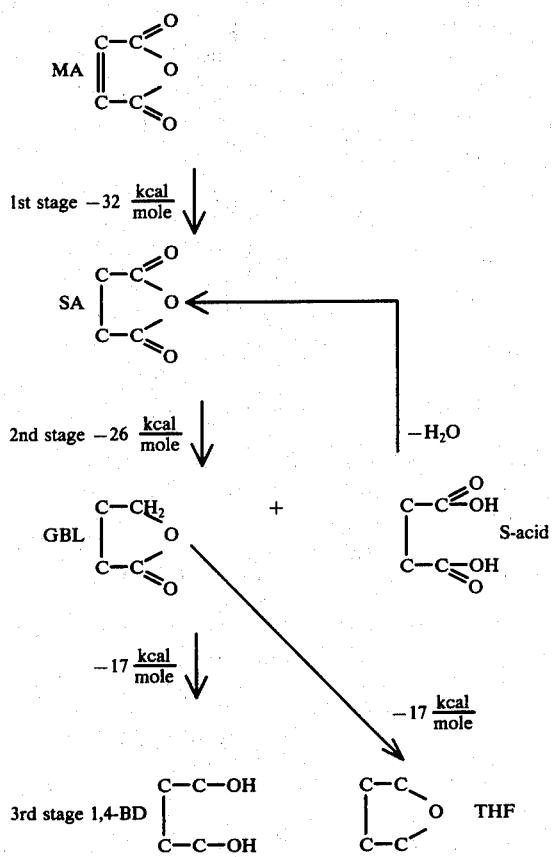

The principle of such a process has been disclosed, inter alia in U.S. Patent No. 3,492,314 and Bristish Pat. No. 1,226,292. However, as may be seen from the practical Examples in these publications, different mixtures — depending on the hydrogenation catalyst used — of intermediate products and end products, e.g. succinic acid, butyrolactone, tetrahydrofuran and butanediol, as well as propanol, butanol and polymeric esters of the above compounds, are formed It is evident that processes of this type are unsatisfactory since the predominant interest is to obtain materials which are substantially single substances and very pure.

The above patents recommend the use of suspended catalysts based on nickel; catalysts containing copper have also previously been used, as disclosed e.g., in Japanese Patent Publication Nos. 5,366/69 and 40,770/72, though these as a rule only effect the hydrogenation of butyrolactone to tetrahydrofuran or butanediol. According to other sources (e.g. Japanese Patent Publication Nos. 17,259/67 and 17,818/67) the hydrogenation reactions referred to above as 1 and 2 can be carried out with certain copper catalysts and according to one of these proposals the reaction is carried out in the gas phase.

Though the reaction in question has frequently been investigated, a process without side reactions which can be carried out in a continuous plant has not previously been disclosed.

It is an object of the present invention to provide such process, based on the fact that such a process, if it is to give a defined reaction product, presupposes a defined course of the intermediate stages.

The process of the invention comprises the following steps:

a. maleic anydride or succinic anhydride is hydrogenated in the presence of γ-butyrolactone over a fixed-bed catalyst containing nickel, to give γ-butyrolactone, b. the water formed during the hydrogenation is removed by feeding the reaction mixture to the middle section of a distillation column, isolating water and γ-butyrolactone on the one hand, and succinic anhydride and γ-butyrolactone on the other, recycling the succinic anydride and γ-butyrolactone, and separating the γ-butyrolactone and water by distillation, and c. γ-butyrolactone is converted by conventional methods, over a catalyst containing copper, into butanediol and/or tetrahydrofuran.

In order to effect a sharp separation between the hydrogenation of maleic anhydride to succinic anhydride, on the one hand, and of succinic anhydride to butyrolactone, on the other, the method followed is suitably that described in the patents cited above the hydrogenation of maleic anhydride to succinic anhydride being carried out at a relatively low pressure and relatively low temperature and the hydrogenation of succinic anhydride to butyrolactone being carried out under relatively severe conditions, i.e. at a relatively high pressure and relatively high temperature.

Whilst the conventional process present considerable difficulties from the point of view of separation of the two hydrogenation reactions, because of the presence of suspended catalysts and because the transfer of the reaction products, containing solids, from the first hydrogenation stage to conditions of higher pressure and higher temperature is virtually hopeless, such a process can be carried out substantially more simply using fixed catalysts, since the pumps required to generate the higher pressure in the second stage can, under the new conditions, be used without further reservations.

The process avails itself of some aspects of the old concept of carrying out the hydrogenation of maleic anhydride or succinic anhydride to butyrolactone in the presence of excess butyrolactone; if maleic anhydride is used as the raw material, the hydrogenation is divided into two stages; according to a preferred embodiment, a part of the butyrolactone ultimately formed is recycled so as to feed different amounts of butyrolactone to the two preceding hydrogenation reactions. As a result, the hydrogenation of the succinic anhydride is carried out at higher dilution than the hydrogenation of maleic anhydride; solutions of from 10 to 50% strength of succinic anhydride in butyrolactone prove to have a suitable concentration for this stage of the process sequence.

The defined presence of excess butyrolactone in addition to any unreacted succinic anhydride, free succinic acid and water now makes it possible, according to the invention, to remove the water formed during the hydrogenation reaction and at the same time to reconvert the succinic acid, formed from succinic anhydride and water in a side reaction, into succinic anhydride and water.

The reaction mixture obtained is fed to a distillation column so that water and a part of the butyrolactone are obtained as the overhead product and succinic anhydride and the remainder of the butyrolactone are obtained as the bottom product; the succinic acid fed in is completely converted.

The bottom product obtained can be recycled to the reaction in a simple manner, further butyrolactone being added if appropriate. The water contained in the vapor phase is separated, by a further distillation, from the desired butyrolactone, which in turn can be used for conversion to tetrahydrofuran and/or butanediol.

The butyrolactone which according to the above description is ultimately obtained as the sole product can then be further converted to tetrahydrofuran or butanediol by conventional methods. In doing so, it is possible to form one or other of these products predominantly or exclusively, by either using a hydrogenation catalyst containing copper and zinc oxide or zinc hydroxide, in which case butanediol is formed preferentially, or using a copper catalyst with an aluminum oxide carrier, in which case tetrahydrofuran is formed preferentially.

The following should be noted regarding details of the catalysts, and process steps, employed. According to the invention, the hydrogenation of maleic anhydride or succinic anhydride is carried out over a fixed-bed nickel catalyst. Nickel catalysts suitable for use in a fixed bed usually employ a carrier such as aluminum oxide, silicon dioxide, magnesium silicate, aluminum silicate, titanium dioxide, zirconium dioxide or the like, or are unsupported catalysts. They may contain conventional activators and deactivators and other assistants, e.g. graphite, stearic acid or hydraulic binders. A particularly suitable catalyst for the process of the invention, in which the two hydrogenation stages take place under different conditions, is disclosed, e.g., in German Pat. No. 2,024,282.

For the hydrogenation of maleic anhydride, suitable conditions to be maintained are a temperature of from 100° to 200° C, especially from 120° to 180° C, and a hydrogen pressure of up to 300 bars, preferably up to 50 bars.

The hydrogenation of succinic anhydride to butyrolactone is in general carried out at a temperature of from 100° to 250° C, especially from 120° to 200°, which is in general from 20° to 50° above the temperature used for the preceding hydrogenation. A suitable pressure to use is in general up to 300 bars, especially from 80 to 280 bars.

According to the invention, the separation of the reaction mixture obtained on hydrogenation of succinic anhydride, with simultaneous conversion of the succinic acid by-product to the anhydride, is effected by distillation. This may be carried out, e.g., in a column which suitably has from five to 20 theoretical plates; in general, the reaction mixture is fed in between the second and the 15th plate. Dehydration can also be effected by heating the mixture in a stirred kettle under reflux, whilst removing the water formed.

The dehydrated butyrolactone can now be directly subjected to a final purification and isolation; however, in general the butyrolactone is converted to 1,4-butanediol and/or tetrahydrofuran. For this purpose, the process described above is followed by at least one further hydrogenation stage which exhibits the following features: if it is preferred to obtain butanediol, a copper catalyst, which also contains zinc hydroxide or zinc oxide, is generally used. For example, suitable catalysts may be prepared by precipitating, from solutions containing copper and zinc, mixed crystals which crystallographically belong to the malachite type $Cu_2(OH)_2CO_3$ or the zinc hydroxide/ carbonate type $Zn_5(OH)_6(CO_3)_2$, then thermally decomposing these mixed crystals and using the decomposition product, as obtained or after suitable molding, as the catalyst. Such catalysts suitably also contain small amounts of aluminum; the preparation of a suitable catalyst is described, e.g., in German Published Application No. 2,132,020.

If it is preferred to obtain tetrahydrofuran, it is particularly advantageous, according to the invention, to use a copper catalyst which in addition essentially contains aluminum oxide and, optionally, minor amounts of magnesium and similar elements. a suitable catalyst of empirical formula $6CuO.Al_2O_3$ is obtained, e.g., by following the instructions of German Pat. No. 2,024,282.

Figure 1:
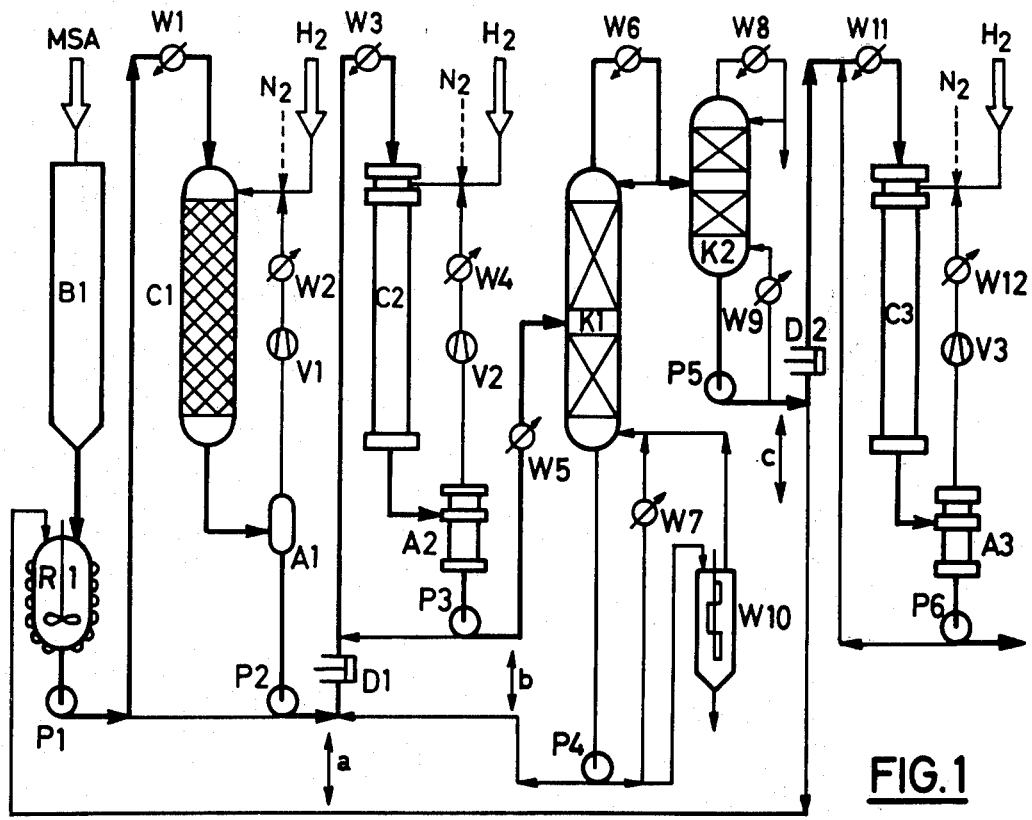
FIG. 1 is a schematic representation of the steps and equipment involved in the process.

The attached flow chart (FIG. 1) particularly clearly illustrates the invention:

Maleic anhydride (MA) passes from the storage tank B1 into a heated stirred kettle R1, where it is dissolved in butyrolactone (GBL). The MA solution is pumped by means of the pump P1 through a heat exchanger of W1 into the first hydrogenation reactor C1. A part of the reaction product is circulated, starting from the separator A1, by means of the circulating pump P2. The hydrogen is also circulated, via the compressor V1 and the heat exchanger W2.

The pump D1 feeds the solution of succinic anhydride (SA) in GBL via the heat exchanger W3 into the second hydrogenation stage, which is carried out at a higher pressure than the first stage. Here again, a part of the liquid is circulated by means of the pump P3 in order to discharge (excess) heat. Hydrogen is also recycled via the compressor V2 and the heat exchanger W4. The reaction mixture then passes into the succinic acid decomposition stage K1, where GBL and water are obtained at the top, and this mixture is separated in the column K2. The pump D2 feeds pure butyrolactone into the reactor C3, where it is hydrogenated to butanediol, with product recycling via P6. The hydrogenation product is distilled in the reduced pressure distillation unit K3 and passes into the container B2 as pure butanediol. When manufacturing THF, the procedure is in principle exactly the same, but different catalyst is used.

A great advantage of the process is that reaction product can be discharged, and products can also be fed in, at the points $a$, $b$ and $c$ marked with double-headed arrows. At $a$ succinic anhydride can be added or isolated. The process can also be used for the manufacture of butyrolactone, if product is discharged at point $c$. The process is economically particularly attractive as a result of this ability to feed in products and discharge products, at various points in the process.

MANUFACTURE OF THE CATALYST

The catalyst preferred for stages 1 and 2 of the process according to the invention is obtained from the catalyst intermediate $Ni_6Al_2(OH)_{16}CO_3.4H_2O$. This catalyst is substantially more active than commercial catalysts, even at low temperatures. As a result of operating below 200° C, the formation of objectionable by-products is largely prevented.

The catalyst intermediate is prepared by precipitation from a 1–2 molar aqueous nickel nitrate solution with 1–2 molar alkali metal carbonate solution, preferably sodium solution, at from 50° to 95° C, preferably at 80° C. During the precipitation, the pH is kept at from 5.0 to 8.0. After the precipitation, the catalyst intermediate is filtered off and washed. the washed product is dried at from 100° to 150° C, preferably at 110° C, and is then calcined at from 300° to 600° C, preferably from 350° to 500 C. The calcined product is mixed with 2% by weight of graphite and then molded to form pellets. The latter are reduced at from 300° to 600° C, preferably at from 400° to 450° C, and then passivated.

SPECIAL INSTRUCTIONS FOR THE MANUFACTURE OF THE CATALYST FOR THE FIRST AND SECOND HYDROGENATION STAGES

To precipitate the compound $Ni_6Al_2(OH)_{16}CO_3.4H_2O$, the following solutions are prepared (Recipe 1):

Solution 1:

279.4 kg of $Ni(NO_3)_2.6H_2O$ and
120.04 kg of $Al(NO_3)_3.9H_2O$
are dissolved in $H_2O$ to give a total volume of solution of 640 l.

Solution 2:

159.00 kg of technical-grade sodium carbonate are dissolved in $H_2O$ to give 750 l to 2 molar solution. Sufficient water is initially introduced into the precipitation vessel to enable the stirrer to operate reasonably. Both solutions, and the water in the precipitation vessel, are separately heated to 80° C. The precipitation is carried out at 80° C and a pH of from 5.0 to 8.0, by simultaneous introduction of the solutions 1 and 2. The pH is regulated by the speed of addition of the solutions. After completion of the precipitation, the mixture is stirred for a further 15 minutes at 80° C and the precipitate is then filtered off, and washed until nitrate is no longer detectable in the filtrate. As a check, a sample of the precipitate is subjected to X-ray analysis to ascertain whether the catalyst intermediate has been produced in a pure form. The amount of the washed precipitate is from 600 to 700 liters. The filter cake is dried at 110° C, giving about 25% by weight of dry product (150 to 175 kg).

After drying, the catalyst intermediate is decomposed for 5 hours at 350° C, to give the oxide mixture. This decomposition results in a further weight loss of about 30%, so that ultimately from 100 to 120 kg of catalyst are obtained. The product is then mixed with 2% by weight of graphite and molded to give 5 × 5 mm pellets. These are reduced with pure hydrogen at 450° C and then passivated at room temperature in a stream of nitrogen into which a small amount of air is introduced. The amount of air introduced is such that the temperature in the reactor does not exceed 50° C.

MANUFACTURE OF A COPPER CATALYST FOR THE HYDROGENATION OF GBL TO BUTANEDIOL (RECIPE 2)

To carry out the precipitation, the following two solutions are first prepared:

Solution 1

7.200 kg of $Cu(NO_3)_2.3H_2O$
11.370 kg of $Zn(NO_3)_2.6H_2O$ and
1.473 kg of $Al(NO_3)_3.9H_2O$
are dissolved in water and made up to a volume of 36 l.

Solution 2

37 l of aqueous solution are prepared from
7.850 kg of technical-grade (anhydrous) sodium carbonate.

The precipitation is carried out in a stirred kettle into which 10 l of water at 80° C are first introduced. The compound is precipitated by simultaneously running in solutions 1 and 2 with vigorous stirring. The pH in the precipitation vessel is adjusted to 7.0 during the precipitation by adjusting the speeds of addition of the solutions. After completion of precipitation, the mixture is stirred for a further 15 minutes and the precipitate produced is then filtered off and washed free from nitrate. The filter cake is dried at 110 C and is then calcined for 5 hours at from 250° C to 270° C. The product obtained is comminuted to a particle size of less than 1 mm, mixed with 2% by weight of graphite and molded to give 5 × 5 mm pellets.

COPPER CATALYST FOR THE HYDROGENATION OF GBL TO THF (RECIPE 3)

The compound $Cu_6Al_2(OH)_{16}CO_3.4H_2O$ is used as the catalyst intermediate. To precipitate this hydroxide-carbonate, the following solutions are first prepared:

Solution 1

23.200 kg of $Cu(NO_3)_2.3H_2O$ and
12.004 kg of $Al(NO_3)_3.9H_2O$
are dissolved in water and made up to a volume of 64 l.

Solution 2

15.270 kg of technical-grade (anhydrous) sodium carbonate are dissolved to give 72 l of an aqueous solution.

The precipitation is carried out in a stirred kettle in which 20 l of water are first heated to 80° C. Solutions 1 and 2 are also heated to 80° C. The precipitation is carried out by running solutions 1 and 2 simultaneously into the well-stirred water. The solutions are run in through rotary flow meters and valves, by means of which the rates of addition are regulated so as to maintain a pH of 6.0 during the precipitation. When solutions 1 and 2 have been run in, the pH is brought to 7.0 with sodium carbonate and the mixture is stirred for a further 15 minutes. The precipitate is filtered off and washed free from nitrate. A sample of the precipitate is subjected to X-ray analysis. The moist filter cake is then dried at 110° C after which it is calcined for 5 hours at 300° C. The calcination product, crushed to <1.5 mm and mixed with 2% by weight of graphite, is molded to give 5 × 5 mm pellets.

EXAMPLE 1

Three reactors were used to carry out the process. To hydrogenate MA to SA, a reactor was filled with nickel catalyst described initially. The same catalyst was also used in the 2nd reactor for the hydrogenation of SA to BTL. Before starting the reaction, the passivated catalyst, in both reactors, was reduced with hydrogen at 200° C. After the reduction, a 10% strength solution of MA in butyrolactone was fed into reactor 1. The solution was introduced at the top of the reactor, through a liquid distributor, to ensure that the catalyst was exposed to the liquid as uniformly as possible. Reactor 1 was operated at a hydrogen pressure of from 5 to 25 bars. The reaction mixture was then fed into the second reactor by means of a pump, and in this reactor the SA was hydrogenated to GBL under a higher pressure. In the pilot plant, hydrogen was not circulated, but a certain amount was constantly discharged as off-gas. The table which follows summarizes the experimental results (STY = space-time yield).

TABLE 1

Reactor I, MA → SA

| Solution % MA | H₂ pressure bar | Temp. ° C | H₂ off-gas Nl/hr | STY kg of SA 1 of catalyst.hr |
| --- | --- | --- | --- | --- |
| 10 | 5 | 150 | 200 | 0.550 |
| 10 | 25 | 150 | 200 | 0.830 |
| 10 | 5 | 180 | 200 | 0.670 |

Reactor II, SA → BTL

| Solution | H₂ pressure bar | Temp. ° C | H₂ off-gas Nl/hr | STY kg of BTL 1 of catalyst.hr |
| --- | --- | --- | --- | --- |
| 10 | 150 | 150 | 200 | 0.230 |
| 10 | 150 | 180 | 200 | 0.350 |
| 10 | 250 | 180 | 200 | 0.520 |

The product from the second hydrogenation stage is now heated under reflux in a column so as to decompose the succinic acid, which has been formed, to the anhydride and $H_2O$. Butyrolactone and water are taken off at the top of the column and separated in a second distillation stage. The butyrolactone obtained is dissolved in butanediol and hydrogenated to butanediol in the third hydrogenation stage. For this purpose, the trickle reactor is filled with catalyst prepared according to Instruction 2. The catalyst is reduced with a nitrogen/hydrogen gas mixture (containing from 1 to 2% by volume of $H_2$) at from 150° to 250° C. After the reduction, the hydrogenation is carried out at a higher pressure, with trickle feed, analogously to the other two hydrogenation stages. The Table which follows shows the space-time yield of butanediol under various conditions.

| Solution % GBL | H₂ partial pressure [bar] | Temp. ° C | Amount of H₂ off-gas Nl/hr | STY kg of BD/ 1 of catalyst.hr |
| --- | --- | --- | --- | --- |
| 10 | 250 | 170 | 200 | 0.410 |
| 30 | 250 | 180 | 200 | 0.900 |
| 40 | 150 | 175 | 200 | 0.508 |
| 20 | 150 | 195 | 200 | 0.550 |
| 20 | 150 | 170 | 200 | 0.360 |

EXAMPLE 2 (PART-REACTION)

350 ml of the copper catalyst prepared according to Recipe 3 were filled into a vertical high pressure tubular reactor and reduced at from 100° to 200° C using a nitrogen/hydrogen mixture containing 98% of $N_2$ and 2% of $H_2$. A 10% strength solution of butyrolactone in butanediol was now passed over the catalyst from the bottom of the reactor and the butyrolactone was hydrogenated under a hydrogen pressure of 250 bars, at from 150° to 200° C. The throughput was 1 l of solution per hour, corresponding to 2.86 1/l of catalyst.hr.

Figure 2:
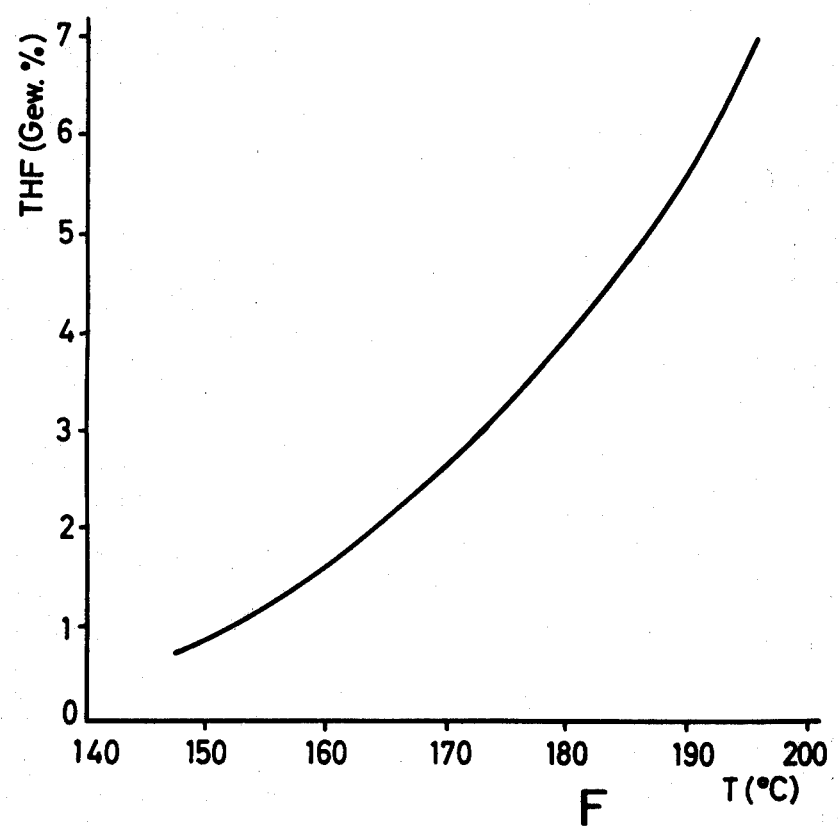
FIG. 2 is a graph showing the weight percent THF produced at various temperatures using the catalyst of recipe 3.

This treatment converted the butyrolactone into butanediol and THF. The amount of THF formed depends greatly on the temperature. FIG. 2 shows the amount of THF in % by weight as a function of the temperature.

The catalyst prepared according to Recipe 2 was also tested under the same reaction condtions. At temperatures below 190° C, butanediol is formed if this catalyst is used, whilst the THF content of the reaction product at the stated temperature is less than 0.1%.

We claim:

1. A process for the manufacture of 1,4-butanediol and/or tetrahydrofuran by catalytic hydrogenation of maleic anhydride and/or succinic anhydride (in the former case via succinic anhydride), with formation of γ-butyrolactone as an intermediate, wherein the improvement consists in
   a. hydrogenating maleic anhydride or succinic anhydride in the presence of γ-butyrolactone over a catalyst containing nickel, to give γ-butyrolactone,
   b. removing the water formed during the hydrogenation by separating γ-butyrolactone and water from succinic anhydride by distillation, recycling succinic anhydride and separating γ-butyrolactone and water by distillation, and
   c. converting γ-butyrolactone into butanediol and/or tetrahydrofuran over a catalyst containing copper.

2. A process as claimed in claim 1, wherein the hydrogenation of maleic anhydride via succinic anhydride to γ-butyrolactone is carried out by converting maleic anhydride to succinic anhydride at relatively low pressure and low temperature and converting succinic anhydride to γ-butyrolactone at relatively high pressure and high temperature.

3. A process as claimed in claim 1, wherein the copper catalyst used is a hydrogenation catalyst containing copper and zinc hydroxide or zinc oxide, and 1,4-butanediol is obtained preferentially.

4. A process as claimed in claim 1, wherein the copper catalyst used contains aluminum and tetrahydrofuran is obtained preferentially.

* * * * *